United States Patent [19]

Holmes et al.

[11] Patent Number: 4,767,871
[45] Date of Patent: Aug. 30, 1988

[54] PYRAZOLIDINIUM YLIDES

[75] Inventors: Richard E. Holmes; Louis N. Jungheim, both of Indianapolis, Ind.

[73] Assignee: Eli Lilly and Company, Indianapolis, Ind.

[21] Appl. No.: 45,011

[22] Filed: Apr. 30, 1987

Related U.S. Application Data

[63] Continuation of Ser. No. 862,912, May 14, 1986, abandoned, which is a continuation-in-part of Ser. No. 728,733, Apr. 30, 1985, abandoned.

[30] Foreign Application Priority Data

Apr. 28, 1986 [EP] European Pat. Off. ......... 86303177.9

[51] Int. Cl.$^4$ .................. C07D 231/50; C07D 403/04
[52] U.S. Cl. ..................................... 548/365; 548/364
[58] Field of Search ................................ 548/364, 365

[56] References Cited

U.S. PATENT DOCUMENTS 4,465,679  8/1985  Huang et al. ...................... 548/365

FOREIGN PATENT DOCUMENTS

| | | | |
|---|---|---|---|
| 64058 | 10/1968 | German Democratic Rep. ........................ | 548/365 |
| 110868 | 1/1975 | German Democratic Rep. ........................ | 548/365 |
| 143617 | 9/1980 | German Democratic Rep. ........................ | 548/365 |
| 1377596 | 12/1974 | United Kingdom ............... | 548/365 |
| 1472052 | 4/1977 | United Kingdom ............... | 548/365 |
| 2073740A | 10/1981 | United Kingdom ............... | 548/365 |

OTHER PUBLICATIONS

M. Ueda, M. Funayama and Y. Imai, *J. Polymer Science Polym. Chem. Ed.*, 15, pp. 1629–1635 (1977).

M. A. Breger, *Antibiotiki*, 16, pp. 26–27 (1961).

H. Dorn and A. Otto, Angew. *Chem. Int. Ed. Engl.*, 7, pp. 214–215 (1968).

H. Dorn and A. Otto, *Chem. Ber.*, 101, pp. 3287–3301 (1968).

H. Dorn and A. Zubek, *Z. Chem.*, 8, pp. 270–271 (1968).

G. Geissler, K. Angermuller, I. Behning, S. Furneisen, W. Fust, M. Hippius, B. Muller, G. Schauer, H. Slezak and G. Tomascheswki, *Z. Chem.*, 21, pp. 356–375 (1981).

E. C. Taylor, Neil F. Haly and Robert J. Clemens, *J. Amer. Chem. Soc.*, 103, pp. 7743–7752 (1981).

Chem. Abstracts, vol. 57, No. 3, 8/6/62, col. 3434d–g, N. K. Kochetov et al., ZH. OBSHCH. KHIM. 31, 3292–8 (1961).

*Primary Examiner*—Mary C. Lee
*Assistant Examiner*—Kurt G. Briscoe
*Attorney, Agent, or Firm*—Paul C. Steinhardt; Leroy Whitaker

[57] ABSTRACT 4-(Protected amino)-3-oxo-1-(substituted and unsubstituted methylene)-1,2-pyrazolidinium ylides are intermediates to 7-substituted bicyclic pyrazolidione antimicrobials.

17 Claims, No Drawings

PYRAZOLIDINIUM YLIDES

This application is a continuation, of application Ser. No. 862,912, filed May 14, 1986, now abandoned, which in turn is a continuation-in-part of L. N. Jungheim U.S. Pat. application Ser. No. 728,733, filed Apr. 30, 1985, now abandoned.

SUMMARY OF THE INVENTION

The invention provides pyrazolidinium ylide compounds of the formula

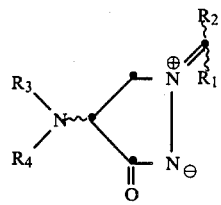

wherein $R_1$, $R_2$, $R_3$ and $R_4$ are defined below. The pyrazolidium ylide compounds are intermediates in the synthesis of 7-substituted bicyclic pyrazolidinone antimicrobials.

DETAILED DESCRIPTION OF THE INVENTION

The present invention embraces compounds of the Formula 1:

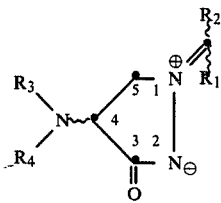

The compounds of Formula 1 are referred to herein as a "pyrazolidinium ylide" or more succintly, as an "ylide" compound. The numbering system for the ylide is denoted in Formula 1.

In the above Formula, the undulating line symbol "" indicates that the amino group attached to position 4 of the ylide could be in the R or S configuration and, when $R_1$ and $R_2$ are different, indicates that either one could be in the E or Z configuration. Formula 1 also embraces various percentage mixtures of the possible stereoisomers at position 4 and/or at the doubly-bonded substituted methylene group.

In the above Formula 1:

$R_1$ and $R_2$ are the same or different and are hydrogen, $C_1$ to $C_2$ alkyl, $C_1$ to $C_6$ substituted alkyl, $C_7$ to $C_{12}$ arylalkyl, $C_7$ to $C_{12}$ substituted arylalkyl, phenyl, substituted phenyl or a group of the formula

—COOR$_5$ wherein $R_5$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, a carboxyprotecting group, or a non-toxic, metabolically-labile ester-forming group; and $R_3$ and $R_4$ are (1) taken together to form a phthalimido group; or (2) either $R_3$ or $R_4$ is hydrogen and the other of $R_3$ or $R_4$ is an amino-protecting group.

In the above Formula 1, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_1$ to $C_6$ substituted alkyl" dnotes the above $C_1$ to $C_6$ alkyl groups that are substituted by one or two halogen, hydroxy, protected hydroxy, protected amino, $C_1$ to $C_7$ acyloxy, nitro, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-acetoxy(isopropyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl), acetoxymethyl, carbamoyloxymethyl, chloromethyl, bromomethyl and iodomethyl.

The term "$C_1$ to $C_4$ alkoxy" as used herein denotes groups such as methoxy, ethoxy, n-propoxy, isopropoxy, n-butoxy, t-butoxy and like groups. Similarly, the term "$C_1$ to $C_7$ acyloxy" denotes herein groups such as formyloxy, acetoxy, propionyloxy, butyryloxy, pentanoyloxy, hexanoyloxy, heptanoyloxy, and the like.

The term "substituted phenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, protected carboxy, carboxymethyl, protected carboxymethyl, hydroxymethyl, protected hydroxymethyl, protected aminomethyl, trifluoromethyl or methylsulfonylamino.

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl, a mono- or di(protected carboxy) phenyl group such as 2,4-di(protected carboxy)phenyl, a mono- or di(hydroxymethyl)phenyl or (protected hydroxymethyl)phenyl such as 3-(protected hydroxymethyl)phenyl or 3,4-di(hydroxymethyl)phenyl, a mono- or di(-protected aminomethyl)phenyl such as 2,4-(protected aminomethyl)phenyl, or a mono- or di(methylsulfonylamino)phenyl such as 3-(methylsulfonylamino)phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-(protected amino)methylphenyl and the 3-(methylsulfonylamino)phenyl groups.

The terms "halo" and "halogen" refer to fluoro, chloro, bromo or iodo groups.

The term "$C_7$ to $C_{12}$ arylalkyl" denotes a $C_1$ to $C_6$ alkyl group substituted at any position by a phenyl ring. Examples of such a group include phenyl methyl(benzyl), 2-phenylethyl, 3-phenyl-(n-propyl), 4-phenylhexyl, 3-phenyl-(n-amyl), 3-phenyl-(sec-butyl) and the like. A preferred group is the benzyl group.

The term "$C_7$ to $C_{12}$ substituted arylalkyl" denotes a $C_7$ to $C_{12}$ substituted arylalkyl group substituted on the $C_1$ to $C_6$ alkyl portion with one or two groups chosen from halogen, hydroxy, protected hydroxy, protected amino, $C_1$ to $C_7$ acyloxy, nitro, protected carboxy, carbamoyl, carbamoyloxy, cyano, methylsulfonylamino or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, protected carboxy, protected carboxymethyl, hydroxymethyl, protected hydroxymethyl, protected aminomethyl, or a methylsulfonylamino group. As before, when either the $C_1$ to $C_6$ alkyl portion or the phenyl portion or both are disubstituted, the substituents can be the same or different.

Examples of the term "$C_1$ to $C_{12}$ substituted arylalkyl" include groups such as 2-phenyl-l-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-(protected aminobenzyl), 6-(4-methoxyphenyl)-3-carboxy(n-hexyl), 5-(4-(protected amino)methyl phenyl)-3-(protected amino)methyl)(n-pentyl), and the like.

The compounds of Formula 1 may also exist as the solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The terms "carboxy-protecting group" and "protected carboxy" as used in the specification refer to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the ylide molecule and can be removed at the appropriate point without disrupting the remainder of the ylide molecule or the bicyclic pyrazolidinone molecules for which the instant ylides are intermediates. In particular, it is important not to subject the carboxy-protected ylide or bicyclic pyrazolidinone molecules to strong nucleophilic bases or to reductive conditions employing highly activated metal catalysts such as Raney nickel. (Such harsh removal conditions are also to be avoided when removing the amino-protecting groups and the hydroxy-protecting groups discussed below.) A preferred carboxylic acid protecting group is the allyl group. Similar carboxy-protecting groups used in the cephalosporin, penicillin and peptide arts can also be used to protect a carboxy group substituent of the ylides. Further examples of these groups are found in E. Haslam, "Protective Groups in Organic Chemistry" J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The terms "protected hydroxy" and "hydroxy-protecting group" refer to readily cleavable groups bonded to hydroxyl groups, such as the tetrahydropyranyl, 2-methoxyprop-2-yl, 1-ethoxyeth-1-, methoxymethyl, $\beta$-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl and 2,2,2-trichloroethoxycarbonyl groups, and the like.

The species of hydroxy-protecting is not critical so long as the derivatized hydroxyl group is stable to the conditions of subsequent reaction(s) and can be removed at the appropriate point without disrupting the remainder of the ylide molecule or the bicyclic pyrazolidinone molecules.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy protecting groups are the trityl group and the tetrahydropyranyl group.

The terms "amino-protecting group" and "protected amino" as used in the specification refer to substituents of the amino group commonly employed to block or protect the amino functionality while carrying out reactions at other functional groups on the compound. Examples of such amino-protecting groups include the formyl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xylyl)iso-propoxycarbonyl, 1,1-diphenyleth-1-yloxycarbonyl, 1,1-diphenylprop-1-yloxy-carbonyl, 2- phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like, the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the ylide molecule and can be removed at the appropriate point without disrupting the remainder of either the ylide molecule or the bicyclic pyrazolidinone molecules. Preferred amino-protecting groups are the allyloxycarbonyl, the t-butoxycarbonyl and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl and $\alpha$-methoxyethyl; the $\alpha$-($C_1$ to $C_4$)alkoxyethyl groups, for example methoxyethyl, ethoxyethyl, propoxyethyl, iso-propoxyethyl, and the like; the 2-oxo-1,3-dioxolenyl-4-methyl groups, such as 5-methyl-2-oxo-1,3-dioxolenylmethyl, 5-phenyl-4-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, $\alpha$-acetoxymethyl, and the like; the ethoxycarbonyl-1-methyl group; the $\alpha$-acyloxy-$\alpha$-substituted methyl groups, for example $\alpha$-acetoxyethyl, the 3-phthalidyl or 5,6-dimethylphthalidyl groups, the 1-($C_1$ to $C_4$ alkyloxycarbonyloxy)eth-1-yl groups such as the 1-(ethoxycarbonyloxy)ethyl group; and the 1-($C_1$ to $C_4$ alkylaminocarbonyloxy)ethyl-1-groups such as the 1-(methylaminocarbonyloxy)eth-1-yl group.

One of two preferred groups of the compounds of Formula 1 are when $R_1$ and $R_2$ are the same or different and are hydrogen, $C_1$ to $C_6$ alkyl or $C_1$ to $C_6$ substituted alkyl and which are a mixture of 4-(R) and 4-(S) stereoisomers. The preferred group contains a further preferred group of compounds wherein $R_1$ and $R_2$ are the same and are hydrogen or $C_1$ to $C_6$ alkyl. Two preferred groups of this latter group of compounds occur when $R_1$ and $R_2$ are the same and are either hydrogen (the "unsubstituted methylene ylides") or methyl (the "dimethylmethylene ylides").

A preferred group of unsubstituted methylene ylides and also of dimethylmethylene ylides are represented when either $R_3$ or $R_4$ is hydrogen and the other is an amino-protecting group. Examples of such compounds include:

4-(R,S)-(t-butoxycarbonylamino)-3-oxo-1-methylene-1,2-pyrazolidinium ylide;

4-(R,S)-(allyloxycarbonylamino)-3-oxo-1-methylene-1,2-pyrazolidinium ylide;

4-(R,S)-(trimethylsilylamino)-3-oxo-1-methylene-1,2-pyrazolidinium ylide;

4-(R,S)-(benzyloxycarbonylamino)-3-oxo-1-methylene-1,2-pyrazolidinium ylide;

4-(R,S)-(tritylamino)-3-oxo-1-methylene-1,2-pyrazolidinium ylide;

4-(R,S)-(2,2,2-trichloroethoxycarbonylamino)-3-oxo-1-methylene-1,2-pyrazolidinium ylide;

4-(R,S)-(2-(trimethylsilyl)ethyloxycarbonyl)-3-oxo-1-methylene-1,2-pyrazolidinium ylide;

4-(R,S)-(trichloroacetylamino)-3-oxo-1-methylene-1,2-pyrazolidinium ylide;

4-(R,S)-(bromoacetylamino)-3-oxo-1-methylene1,2-pyrazolidinium ylide;

4-(R,S)-(2-nitrobenzylsulfenamido)-3-oxo-1-methylene-1,2-pyrazolidinium ylide;

4-(R,S)-(t-butoxycarbonylamino)-3-oxo-1-(dimethylmethylene)- 1,2-pyrazolidinium ylide;

4-(R,S)-(allyloxycarbonylamino)-3-oxo-1-(dimethylmethylene)-1,2-pyrazolidinium ylide;

4-(R,S)-(trimethylsilylamino)-3-oxo-1-(dimethylmethylene)-1,2-pyrazolidinium ylide;

4-(R,S)-(benzyloxycarbonylamino)-3-oxo-1-(dimethylmethylene)-1,2-pyrazolidinium ylide;

4-(R,S)-(tritylamino)-3-oxo-1-(dimethylmethylene)-1,2-pyrazolidinium ylide;

4-(R,S)-(2,2,2-trichloroethoxycarbonylamino)-3-oxo-1-(dimethylmethylene)-1,2-pyrazolidinium ylide;

4-(R,S)-(2-(trimethylsilyl)ethyloxycarbonyl)-3-oxo-1-(dimethylmethylene)-1,2-pyrazolidinium ylide;

4-(R,S)-(trichloroacetylamino)-3-oxo-1-(dimethylmethylene)-1,2-pyrazolidinium ylide;

4-(R,S)-(bromoacetylamino)-3-oxo-1-(dimethylmethylene)-1,2-pyrazolidinium ylide; and 4-(R,S)-(benzoylmethylsulfonamido)-3-oxo-1-(dimethylmethylene)-1,2-pyrazolidinium ylide.

A more preferred group of both unsubstituted methylene ylide and dimethylmethylene ylide compounds is:

4-(R,S)-(t-butoxycarbonylamino)-3-oxo-1-methylene-1,2-pyrazolidinium ylide;

4-(R,S)-(allyloxycarbonylamino)-3-oxo-1-methylene-1,2-pyrazolidinium ylide;

4-(R,S)-(t-butoxycarbonylamino)-3-oxo-1-(dimethylmethylene)-1,2-pyrazolidinium ylide; and 4-
-(R,S)-(allyloxycarbonylamino)-3-oxo-1-(dimethylmethylene)-1,2-pyrazolidinium ylide;

with the two 4(R,S)-(t-butoxycarbonylamino) compounds being a most preferred group.

The second of the two preferred groups of compounds of Formula 1 are the 4-(S) stereoisomers and have the formula

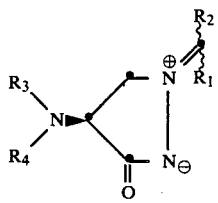

wherein $R_1$, $R_2$, $R_3$ and $R_4$ are as described above for the Formula. A more preferred group of the 4(S) stereoisomers occurs when $R_1$ and $R_2$ are each hydrogen, and especially so when either $R_3$ or $R_4$ is hydrogen and the other is an amino-protecting group. Examples of this latter group of compounds include:

4-(S)-(t-butoxycarbonylamino)-3-oxo-1-methylene-1,2-pyrazolidinium ylide;
4-(S)-(allyloxycarbonylamino)-3-oxo-1-methylene-1,2-pyrazolidinium ylide;
4-(S)-(trimethylsilylamino)-3-oxo-1-methylene-1,2-pyrazolidinium ylide;
4-(S)-(benzyloxycarbonylamino)-3-oxo-1-methylene-1,2-pyrazolidinium ylide;
4-(S)-(tritylamino)-3-oxo-1-methylene-1,2-pyrazolidinium ylide;
4-(S)-(2,2,2-trichloroethoxycarbonylamino)-3-oxo-1-methylene-1,2-pyrazolidinium ylide;
4-(S)-(2-(trimethylsilyl)ethyloxycarbonyl)-3-oxo-1-methylene-1,2-pyrazolidinium ylide;
4-(S)-(trichloroacetylamino)-3-oxo-1-methylene-1,2-pyrazolidinium ylide;
4-(S)-(bromoacetylamino)-3-oxo-1-methylene-1,2-pyrazolidinium ylide; and
4-(S)-(2-nitrobenzylsulfenamido)-3-oxo-1-methylene-1,2-pyrazolidinium ylide.

A most preferred group of the latter more preferred group of 4-(S)-stereoisomers are:
4-(S)-(t-butoxycarbonylamino)-3-oxo-1-methylene-1,2-pyrazolidinium ylide; and
4-(S)-(allyloxycarbonylamino)-3-oxo-1-methylene-1,2-pyrazolidinium ylide;

with the 4-(S)-(t-butoxycarbonylamino) compound being the most preferred compound.

One synthesis of pyrazolidinium ylide compounds of the instant invention is depicted below in Scheme 1. The products in the synthesis of the Scheme are mixtures of 4-(R) and 4-(S) stereoisomers.

Scheme 1

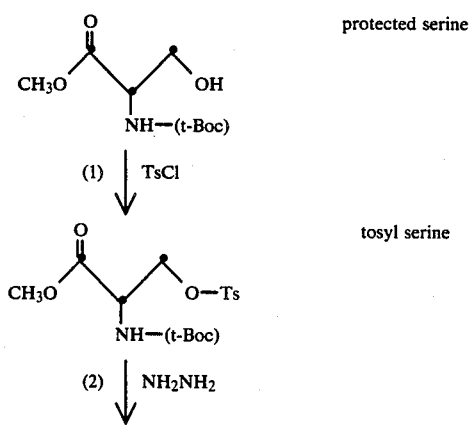

-continued
Scheme 1

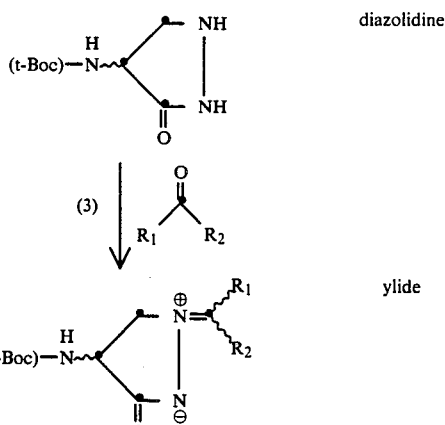

The above Scheme depicts the synthesis of a 4-(R,S)-(t-butoxycarbonylamino) ylide. Ylide starting materials with different amino protecting groups are obtained from serine derivatized with a protecting group other than t-butoxycarbonyl.

The first step in the synthesis of the ylide compounds, represented by Reaction 1 in the above Scheme, is the tosylation of the hydroxy group of the protected serine derivative. The tosylation is carried out in methylene chloride with p-toluenesulfonyl chloride in the presence of a catalytic amount of 4-dimethylaminopyridine and greater than one equivalent of pyridine. The reaction mixture is stirred at room temperature overnight.

The tosylated serine obtained is cyclized to give the diazolidine. The cyclization represented by Reaction 2 is carried out by adding the tosyl serine to a solution of 97% hydrazine in methylene chloride under nitrogen. The mixture is then stirred at room temperature for five hours.

The final reaction in the synthesis of the stereoisomeric mixture of pyrazolidinium ylide intermediates comprises the condensation of a ketone or an aldehyde with a diazolidine to give the pyrazolidinium ylide. As a useful alternative procedure, the ketal of the ketone may be condensed with the diazolidine in the presence of an acid. For example, the diazolidine reagent is combined with acetone dimethyl acetal in methanol and then the solution is treated with d-10 camphorsulfonic acid. The mixture is refluxed for 1.5 hours to give the dimethyl ylide (i.e., $R_1$ and $R_2$ are methyl). The unsubstituted ylide (when $R_1$ and $R_2$ are hydrogen) is synthesized by combining the diazolidine reagent and 37% aqueous formaldehyde in methanol and stirring the mixture for twenty minutes at room temperature. When $R_1$ and $R_2$ are different, those skilled in the art will recognize that this final reaction will produce a mixture of E and Z isomers.

The synthesis of the above diazolidine starting materials are further described by L. N. Jungheim and R. E. Holmes in U.S. patent application No. 862,917, filed 4-30-87filed this even date, herein incorporated by reference, which application is in turn a continuation-in-part application of L. N. Jungheim, U.S. patent application No. 728,734, filed Apr. 30, 1985, herein incorporated by reference.

The stereospecific synthesis of which pyrazolidinium ylides of Formula 1 is diagramed below in Scheme 2.

Scheme 2

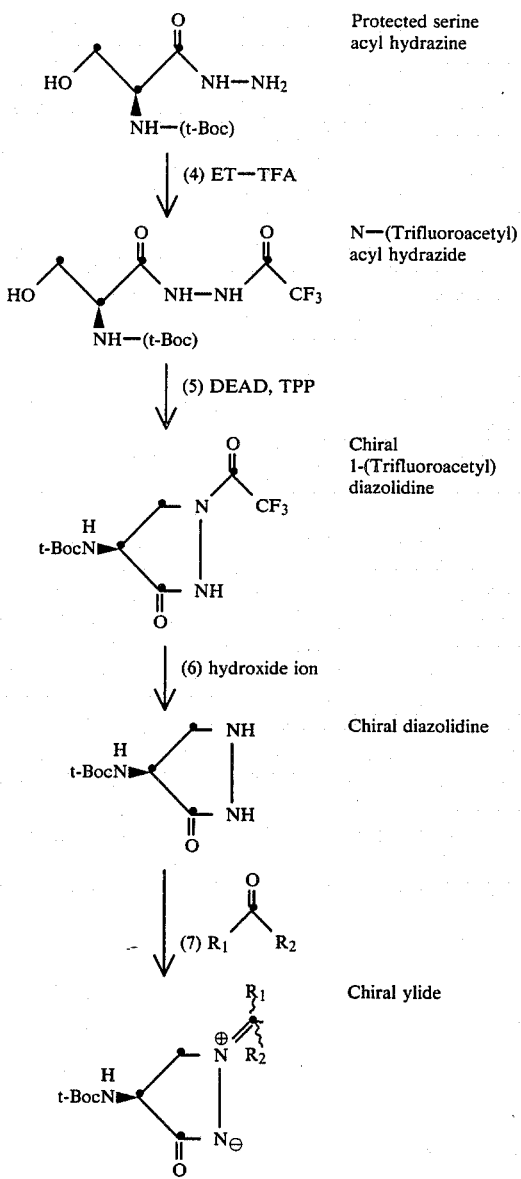

The above Scheme depicts the synthesis of 4-(S)-(t-butoxycarbonylamino) ylide compounds. Ylide compounds with the 4-(R) configuration are synthesized by starting with protected D-serine acyl hydrazide instead of the L-isomer depicted above. Either the 4-(R) or the 4-(S) compounds with amino-protecting groups other than t-butoxycarbonyl are synthesized from a protected serine acyl hydrazide with an amino-protecting group other than t-butoxycarbonyl.

The protected serine acyl hydrazide precursor of Scheme 2 is synthesized in a procedure analogous to B. Iselin and R. Schwyzer, *Helv. Chim. Acta*, 44, p. 169 (1961). The precursor is then acylated with the trifluoroacetyl moiety, as set forth in Reaction 4 in the Scheme. The acylation is carried out in ethanol with an excess of ethylthio trifluorothioacetate ("ET-TFA"). The reaction mixture is stirred at room temperature for 65 hours.

The N-trifluoroacetyl acyl hydrazide obtained is reacted with triphenylphosphine ("TPP") and diethyl azodicarboxylate ("DEAD") as depicted above in Reaction 5. (Although the above Scheme depicts only the use of DEAD, the reaction will also proceed if either dimethyl azodicarboxylate or di(iso-propyl)azodicarboxylate are used).

The stoichiometry of the process of Reaction 5 has the N-(trifluoroacetyl) acyl hydrazide, phosphine and diethyl azodicarboxylate reagent present in at least approximately a 1:1:1 molar ratio. The reaction will proceed in the presence of molar excesses above this ratio of any of the reagents or of the starting material.

The reaction is initiated by first combining (in any order) the solvent, the N-(trifluoroacetyl) acyl hydrazide and the phosphine, and secondly adding the azodicarboxylate reagent.

The reaction temperature of Reaction 5 is not a critical parameter. The process can be carried out at a reaction temperature from approximately the freezing point to approximately the reflux temperature of the solvent. The preferred reaction temperature is approximately room temperature.

The duration of Reaction 5 can be from approximately five minutes to approximately twenty-four hours. The progress of the process can be monitored by standard methods (e.g., thin layer chromatography, high performance liquid chromatography, etc.) The process is stopped when the monitoring method demonstrates that the reaction is substantially complete.

The solvents for the Reaction are aromatic hydrocarbon solvents such as benzene, toluene, xylenes, etc.; ethers such as diethyl ether, tetrahydrofuran, or 1,4-dioxane; chlorinated hydrocarbons such as methylene chloride, chloroform, carbon tetrachloride, dichloroethane, or chlorobenzene; amides such as dimethylformamide and dimethylacetamide; and other solvents such as hexamethylphosphoramide. Tetrahydrofuran is the preferred solvent. It is also desirable, but not essential, to dry and deoxygenate the solvent before use in the process.

The chiral 1-(trifluoroacetyl)diazolidine obtained from Reaction 5 is deacylated with dilute sodium hydroxide solution to yield the chiral 1-(unsubstituted)-diazolidine. The deacylation reaction is represented as Reaction 6 in Scheme 2. The reaction entails generally suspending the chiral 1-(trifluoroacetyl)diazolidine in water then adding at least two equivalents dilute aqueous sodium hydroxide or potassium hydroxide solution. (For instance, a two-fold excess of 1M sodium hydroxide can be used. It is preferred that the initial pH of the solution be from between about 11 to about 12.) The resultant solution is stirred from about 10 minutes to about 3 hours at a temperature from about 10° C. to 25° C. When the reaction is substantially complete the reaction solution is neutralized by the addition of dilute acid, such as 1N hydrochloric acid.

The optimal reaction time for Reaction 6 can be determined by monitoring the progress of the reaction by conventional means such as chromatographic techniques (thin layer chromatography, high performance liquid chromatography, or column chromatography) and spectroscopic methods, alone or in conjunction with chromatographic techniques, such as infrared spectroscopy, nuclear magnetic resonance spectrometry and mass spectrometry. A preferred time period is from between 30 minutes to about 1.5 hours.

The final reaction of Scheme 2, wherein the chiral diazolidines are converted to the chiral pyrazolidinium ylides, is carried out using the conditions described for the analogous reaction (Reaction 3) in Scheme 1.

The ylides of Formula 1 are intermediates to bicyclic pyrazolidinone antimicrobials (and the corresponding intermediates) of the Formula 2.

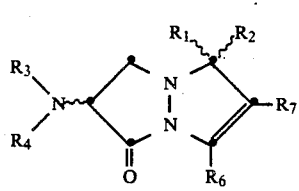

In Formula 2, $R_1$ and $R_2$ are the same as for $R_1$ and $R_2$ in the instant ylides. $R_3$ and $R_4$ in Formula 2 includes all the substituents of $R_3$ and $R_4$ of the instant ylides, plus substituents when either $R_3$ or $R_4$ is hydrogen and the other is an acyl group derived from a $C_1$ to $C_{30}$ carboxylic acid. (Examples of such acyl groups are the acyl groups bonded to the 6- and 7-amino groups of penicillins and cephalosporins, respectively). $R_6$ and $R_7$ in Formula 2 can be a variety of substituents, including a group of the formula $-COOR_5$ wherein $R_5$ means the same as it does for the instant ylide compounds and can also represent hydrogen or an organic or inorganic cation. Further examples of substituents at $R_1$, $R_2$, $R_3$, $R_4$, $R_6$ and $R_7$ in Formula 2 can be found in L. N. Jungheim, S. K. Sigmund, C. J. Barnett, R. E. Holmes and R. J. Ternansky, U.S. patent application No. 862,906filed 4-30-87, filed this even date, herein incorporated by reference, which application is in turn a continuation-in-part of L. N. Jungheim and S. K. Sigmund, U.S. patent application No. 729,021, filed Apr. 30, 1985, herein incorporated by reference.

The bicyclic pyrazolidinones of Formula 2 are synthesized, for example, by various 1,3-dipolar cycloaddition reaction with the instant ylides and a substituted acetylene as shown below in Scheme 3:

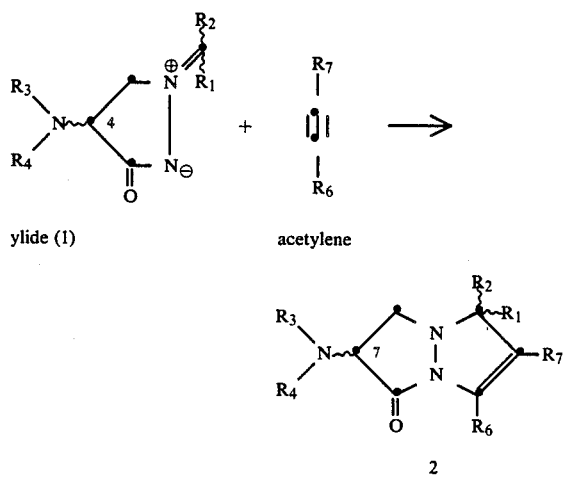

In the above Scheme 3, for brevity's sake, Formula 2 indicates only one of the two possible 2,3-regioisomer products of the reaction. The reaction represented by Scheme 3 can also produce the opposite 2,3-regioisomer as well as a mixture of the regioisomers.

In the above Scheme, $R_1$ and $R_2$ are as defined above for Formula 1, $R_6$ and $R_7$ are as defined for Formula 2 and either $R_3$ or $R_4$ is an amino-protecting group and the other of $R_3$ or $R_4$ is hydrogen. When carrying out the reaction derivative with protecting groups, it is preferable to protect any of the acidic groups represented by $R_1$, $R_2$, $R_6$ or $R_7$. Examples of such acidic groups are the carboxylic acid group and the hydroxyimino group. It is especially preferred that any carboxylic acid groups be protected.

The reaction should be carried out in aprotic solvents. Examples of such solvents are the chlorinated hydrocarbons, the aromatic hydrocarbons and alkyl or aromatic cyano solvents. The preferred solvents for the above reaction are dichloromethane, acetonitrile, and 1,2-dichloroethane.

The temperature for the reaction is not critical. It is preferred that the reaction be carried out between about room temperature to about the reflux temperature of the solvent.

The reaction usually requires a period of about 1 to about 168 hours. The optimal reaction time can be determined by monitoring the progress of the reaction by conventional means such as chromatographic techniques (thin layer chromatography, high performance liquid chromatography, or column chromatography) and/or spectroscopic methods (such as infrared spectroscopy, nuclear magnetic resonance spectrometry and mass spectrometry).

The usual stoichiometry for the reaction is a 1:1 ratio of ylide to acetylene reagent. Of course, an excess of either reagent is permissible. It is preferred that the acetylene reagent be present in excess, and especially preferred that the acetylene be present in a 2:1 excess. Furthermore, the order of addition of either reagent is not critical.

The regiospecificity of the cycloaddition in Scheme 3 is unpredictable. The stereochemical and electronic properties of the ylide and acetylene and the various reaction conditions have as yet yielded no clearly discernable regiospecific trends. Usually the reaction yields widely varying mixtures of 2,3-regioisomer products.

The stereospecificity of the cycloaddition of Scheme 3 at the $C_7$ position of the bicyclic pyrazolidinone is determined by the stereochemistry at the $C_4$ position of the instant ylide intermediates. Thus, a mixture of 4-(R) and 4-(S) stereoisomers of the ylide will yield a corresponding mixture of 7-(R) and 7-(S) stereoisomers of bicyclic pyrazolidinones. Similarly, chiral ylide starting material will yield chiral bicyclic pyrazolidinones. Thus, a 4-(S) ylide will yield the 7-(S) bicyclic pyrazolidinone.

The compounds produced by Scheme 3 above are the 7-(protected amino) compounds of Formula 2 (i.e., when either $R_3$ or $R_4$ is an amino-protecting group and the other of $R_3$ or $R_4$ is hydrogen). In order to enhance the antimicrobial activity of the bicyclic pyrazolidinone compounds, it is necessary to replace the amino-protecting group with an acyl group derived from a $C_1$ to $C_{30}$ carboxylic acid. As discussed above, the acyl groups employed are typically those used to achieve the same purpose when bonded to the 6-amino group of a penicillin or a 7-amino group of a cephalosporin.

The first step for the acylation of a 7-(protected amino) bicyclic pyrazolidinone compounds ("7- protected amino nucleus") is the removal of the amino protecting group. The conditions for the removal of these groups are well known in the cephalosporin and penicillin arts. For example, the trimethylsilyl protecting group is removed by simple hydrolysis. The t-butoxycarbonyl group is removed by acidic hydrolysis (trifluoroacetic acid), and the allyloxycarbonyl group is removed as a palladium complex.

Removal of the acid-labile amino protecting groups usually yields the 7-amino nucleus as a salt. The salt of the nucleus is neutralized by conventional procedures before acylation. For instance, the removal of the t-butoxycarbonyl group with trifluoroacetic acid leaves the trifluoroacetate salt of the resultant 7-amino compound. The salt is taken up in tetrahydrofuran and bis(-trimethylsilyl)trifluoroacetamide is added to yield the corresponding desalinated 7-compound. The neutralized (free amino) compound can be isolated or acylated in situ.

Similarly, the removal of the t-butoxycarbonyl group with a mixture of hydrochloric acid in acetic acid leaves the hydrochloride salt adduct of the bicyclic pyrazolidinone. The hydrochloride adduct is treated with a base such as N-methylmorpholine to yield the 7-amino (neutralized) analog. Conversion of the hydrochloride adduct to the 7-amino compound is usually done in situ.

The methods for the acylation of the neutralized 7-amino bicyclic pyrazolidinone with the acyl side chain are similar to the methods for the acylation of 6-aminopenicillanic acid, 7-aminodesacetoxycephalosporanic acid and 7-aminocephalosporanic acid. One method is to simply combine the 7-amino nucleus with an acid chloride or acid bromide in the presence of an acid scavenger. The acid chloride or acid bromide may be formed in situ. Another method is to combine the 7-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di-(npropyl)carbodiimide, N,N'-di-(iso-propyl)carbodiimide, N,N'-diallylcarbodiimide, N,N'-bis(p-dimethylaminophenyl)carbodiimide, N-ethyl-N'-(4"-ethylmorpholinyl)carbodiimide and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol, may also be used. Dehydrating agents such as phosphorus oxychloride, alkoxyacetylenes and 2-halogenopyridinium salts (such as 2-chloropyridinium methyl iodide, 2-fluoropyridinium methyl iodide, and the like) may be used to couple the free acid or its acid salt with the 7-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenol, 2,4-dinitrophenol, trichlorophenol, pentachlorophenol, N-chlorosuccinimide, N-chloro maleic imide, N-chlorophthalimide, 2-chloro-4,6-dimethoxytriazene, 1-hydroxy-1H-benzotriazole or 1-hydroxy-6-chloro-1H-benzotriazole. The active ester derivatives can also be mixed anhydrides, formed with groups such as methoxycarbonyl, ethoxycarbonyl, iso-butoxycarbonyl, trichloromethylcarbonyl, and iso-but-2-ylcarbonyl and the carboxylic acid of the acyl side chain. The mixed anhydrides are formed by acylating the carboxylic acid of the acyl side chain.

Alternatively, the 7-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (e.g. tetrahydrofuran, acetonitrile, etc.). The resultant EEDQ derivative is used in situ to acylate the 7-amino nucleus.

Once the bicyclic pyrazolidinones are acylated with the appropriate acyl group derived from a $C_1$ to $C_{30}$ carboxylic acid, they are converted to the corresponding antimicrobial final product form by removing any remaining amino, hydroxy and/or carboxy protecting groups on the molecules. As discussed above, such removal methods are well known in the cephalosporin, penicillin and peptide arts. Once the carboxy groups are deprotected, the oral ester may be put on the desired carboxy group(s) at $R_1$, $R_2$, $R_6$ and $R_7$. The methods for making the oral ester derivatives are well known in the cephalosporin and penicillin art.

The antimicrobial compounds of Formula 2 inhibit the growth of certain organisms pathogenic to man and animals. The antimicrobial compounds of Formula 2 are compounds wherein the various amino, hydroxy and/or carboxy protecting groups have been removed. The antimicrobial activity can be demonstrated in vitro using standard tube-dilution techniques. The in vitro tests demonstrate that, in general, the 7-(S) bicyclic pyrazolidinones have better antimicrobial activity than both the corresponding 7-(R) isomers and also a mixture of the two isomers. Representative pathogens which are sensitive to the antimicrobial compounds include *Staphylococcus aureus* X1.1, *Streptococcus pyogenes* C203, *Streptococcus pneumoniae* Park, *Hemophilus influenzae* 76 (ampicillin resistant), *Escherichia coli* N10, *Escherichia coli* EC14, *Escherichia coli* TEM (b-lactamase producer), *Klebsiella pneumoniae* X26, *Klebsiella pneumoniae* KAE (β-lactamase producer), *Klebsiella pneumoniae* X68, *Enterobacter aerogenes* C32, *Enterobacter aerogenes* EB17, *Enterobacter cloacae* EB5 (non-β-lactamase producer), *Salmonella typhi* X514, *Salmonella typhi* B35, *Serratia marcescens* X99, *Serratia marcescens* SE3, *Proteus morganii* PR15, *Proteus inconstans* PR33, *Providencia rettgeri* C24, *Citrobacter freundii* CF17, and the like.

The antimicrobial compounds for which the compounds of this invention are intermediates are useful for the therapeutic or prophylactic treatment of infections in warm-blooded animals caused by gram-positive, gram-negative and acid-fast bacteria.

The antimicrobial compounds can be administered orally, parenterally (e.g. intravenously, intramuscularly or subcutaneously) or as a topical ointment or solution in treating bacterial infections of warm-blooded animals.

Further description of the synthesis and the properties of bicyclic pyrazolidinone antimicrobials and the corresponding intermediates are found in L. N. Jungheim, S. K. Sigmund, C. J. Barnett, R. E. Holmes and R. J. Ternansky, U.S. patent application No. 862,906, filed 4-30-87, filed this even date and in the corresponding parent application (U.S. patent application No. 729,021, filed Apr. 30, 1985).

The following Examples are provided to further illustrate the invention. It is not intended that the invention be limited in scope by reason of any of the following Preparations or Examples.

In the following Preparations and Examples, the terms melting point, nuclear magnetic resonance spectra, field desorption mass spectra, electron impact mass spectra, infra-red spectra, ultraviolet spectra, elemental analysis, high performance liquid chromatography and thin layer chromatography are abbreviated m.p., n.m.r., f.d.m.s., m.s., i.r., u.v., anal., HPLC and TLC, respectively. In addition, the adsorption maxima listed for the i.r. spectra are only those of interest and not all of the maxima observed.

The abbreviations THF, TFA and BSTFA stand for tetrahydrofuran, trifluoroacetate and N,O-bis(trimethylsilyl)trifluoroacetamide, respectively.

In conjunction with the n.m.r. spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d" and "br. t" are broad singlet, doublet and triplet, respectively. "J" indicates the coupling constant in Hertz. "DMSO/$d_6$ is dimethyl sulfoxide where all protons have been replaced with deuterium.

The n.m.r. spectra were obtained on either a Varian Associates EM-390 90 MHz instrument, a Jeol FX-90Q 90 MHz instrument, a Brüker Corp. 270 MHz instrument, or on a General Electric QE-300 300 MHz instrument. The chemical shifts are expressed in δ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on a Cary 118 instrument. Specific rotations were taken on a Perkin-Elmer Q-41 instrument. Thin layer chromatography was carried out on E. Merck silica gel plates. Melting points reported are uncorrected.

EXPERIMENTAL SECTION

Preparation 1

Methyl 3-(p-Toluenesulfonate)-2-(S)-(t-Butoxycarbonylamino)-Propionate

Methyl (3-hydroxy)-2-(S)-(t-butoxycarbonylamino)propionate (58 g, 196 mmol), dry methylene chloride (150 ml), p-toluenesulfonyl chloride (43.35 g, 227.4 mmol), 4-(dimethylamino)pyridine (2.4g, 19.6 mmol) and pyridine (30 ml, 371 mmol) were combined and stirred at room temperature overnight. The reaction solution was concentrated in vacuo to a pale yellow oil. The oil was stored in vacuo overnight, then the white solid that formed was isolated to give 75.33 g of crude product. The product was triturated in petroleum ether (approximately 200 ml) to yield methyl 3-(p-toluenesulfonate)-2-(S)-(t-butoxycarbonylamino)propionate:
n.m.r.: (CDCl$_3$, 90 MHz): δ 7.72, 7.31 (2x dd, 4, aromatic protons), 5.26 (m, 1, nitrogen proton), 4.48(m, 1, C-2 proton), 4.32 (m, 2, C-3 protons), 3.68 (s, 3, methyl protons of methyl ester), 2.4 (s, 3, methyl protons of toluene moiety), 1.40 (s, 9, t-butyl moiety); i.r. (CHCl$_3$): 3435, 3019, 1753, 1711, 1502, 1369, 1351, 1250, 1215, 1190, 1177 cm$^{-1}$; m.s.: 279, 210, 172, 91, 41;

Anal. Calcd. for C$_{16}$H$_{23}$NO$_7$S: Theory: C, 51.19; H, 6.71; N, 3.73; S, 8.54. Found: C, 51.05; H, 6.50; N, 3.63; S, 8.13.

Preparation 2

4-(R,S)-(t-Butoxycarbonylamino)-3-Oxo-1,2-Diazolidine

Under a nitrogen atmosphere, dry methylene chloride (50 ml) was cooled in an ice bath and anhydrous hydrazine (97%, 11.0 g, 333 mmole) was added. The ice bath was removed and the solution was stirred until it warmed to room temperature. At this time a solution of methyl 3-(p-toluenesulfonate)-2-(S)-(t-butoxycarbonylamino)propionate (20.0 g, 53.6 mmole) in dry methylene chloride (50 ml) was gradually added. The reaction solution was stirred under nitrogen at room temperature for 5 hours. The solution was then concentrated under reduced pressure and the concentrate was taken up in saturated aqueous sodium bicarbonate solution. The aqueous solution was continuously extracted for 14hours with methylene chloride (700 ml). The methylene chloride solution was dried over sodium sulfate, filtered and concentrated under reduced pressure to yield approximately 5.15 g, 48% of 4-(R,S)-(t-butoxycarbonylamino)-3-oxo-1,2-diazolidine: n.m.r. (CDCl$_3$, 90 MHz): δ 7.04(m, 1), 5.12 (m, 1), 4.28 (m, 1, C-4-proton), 3.94 (m, 1, C-5 proton), 3.20 (m, 1, C-5 proton), 1.45 (s, 9, t-butyl protons); i.r. (CHCl$_3$) 3430, 3250, 3019, 2983, 1702, 1545, 1503, 1370, 1297, 1241, 1215, 1165 cm$^{-1}$; f.d.m.s.: M$^+$=201;

Anal. Calcd. for C$_8$H$_{15}$N$_3$O$_3$: Theory: C, 47.75; H, 7.51; N, 20.88. Found: C, 47.80; H, 7.56; N, 20.61.

Preparation 3

4-(R,S)-(t-Butoxycarbonylamino)-3-Oxo-1,2-Diazolidine p-Toluenesulfonate Salt 4-(R,S)-(t-Butoxycarbonylamino)-3-oxo-1,2-diazolidine (1.7 g, 8.45mmol) was slurried in methylene chloride (50 ml). p-Toluenesulfonic acid hydrate (1.6 g, 8.45 mmol) was added to the slurry. After 20 minutes the resultant solid material was collected then dried in vacuo for approximately 48 hours to yield 2.95 g of colorless 4-(R,S)-(t-butoxycarbonylamino)-3-oxo-1,2-diazolidine p-toluenesulfonate salt: n.m.r. (90 MHz, DMSO-d$_6$): δ 7.5 (d, 2, J=8), 7.1 (d, 2, J=8), 4.32 (m, 1), 3.9 (m, 1), 3.4 (m, 1) 2.3 (s, 3), 1.4 (s, 9); i.r. (KBr): 1742, 1704, 1537 cm$^{-1}$.

EXAMPLE 1

4-(R,S)-(t-Butoxycarbonylamino)-3-Oxo-1-(Dimethylmethylene)-1,2-Pyrazolidinium Ylide 4-(R,S)-(t-Butoxycarbonylamino)-3-oxo-1,2-diazolidine (2.01 g, 10 mmol) was dissolved in methanol (20 ml). To this solution was added acetone dimethyl acetal (10 mmol) and d-10-camphorsulfonic acid (approx. 5 mg). The mixture was refluxed for 1.5 hours then concentrated in vacuo. The concentrate was recrystallized from dichloromethane/isopropyl ether to give 2.01 g of 4-(R,S)-(t-butoxycarbonylamino)-3-oxo-1-(dimethylmethylene)-1,2-pyrazolidinium ylide: n.m.r. (270 MHz, DMSO-$d_6$): δ 7.2 (d, 1, J=6), 4.54 (t, 1, J=10), 4.28 (m, 1), 3.85 (m, 1), 2.25 (s, 3), 2.18 (s, 3), 1.4(s, 9); i.r. (KBr): 3232, 1692, 1671, 1608 cm$^{-1}$; m.s.: M+=241.

EXAMPLE 2

4-(R,S)-(t-Butoxycarbonylamino)-3-Oxo-1-(Methylene)-1,2-Pyrazolidinium Ylide 4-(R,S)-(t-Butoxycarbonylamino)-3-oxo-1,2-diazolidine (4.02 g, 20 mmol) was dissolved in dry methanol (50 ml). 37% Aqueous formaldehyde (1.62 g, 20 mmol) was added, the mixture was stirred for 20 minutes at room temperature then concentrated in vacuo. The solvent was then removed by several azeotropic distillations with methanol in vacuo at 40° C. The resultant residue was dried in vacuo at 40° C. overnight to yield 4-(R,S)-(t-butoxycarbonylamino)-3-oxo-1-(methylene)-1,2-pyrazolidinium ylide: n.m.r. (90 MHz, CDCl$_3$): δ 6.1–5.3 (m, 2), 4.9–4.2 (m, 6), 4.0–3.6 (m, 2), 3.5–3.1 (m, 2), 1.4 (s, 18); i.r. (KBr): 3379, 2980, 2930, 1705, 1524, 1519, 1504, 1455, 1393, 1368, 1297, 252, 1166 cm$^{-1}$; f.d.m.s.: M$^{\oplus}$=213.

Preparation 4

2,3-di(Allyl Carboxylate)-7-(R,S)-(t-Butoxycarbonylamino)-8-Oxo-1,5-Diazabicyclo[3.3.0]Octa-2-ene 4-(R,S)-(t-Butoxycarbonylamino)-3-oxo-1-(methylene)-1,2-pyrazolidinium ylide from Example 2 above was dissolved in dry acetonitrile (50 ml) and diallyl butynedioate (3.88 g, 20 mmol) was added. The mixture was heated to reflux for 3 hours then concentrated in vacuo. The resultant solid was chromatographed by HPLC on silica gel eluted with 2:1 hexane:ethyl acetate, to yield 2.67 g, 32.8% yield of 2,3-di(allyl carboxylate)-7-(R,S)-(t-butoxycarbonylamino)-8-oxo-1,5-diazabicyclo[3.3.0]octa-2-ene: n.m.r. (90 MHz, CDCl$_3$): δ 6.20–5.70 (m, 2, unsaturated protons on allyl groups), 5.52–5.0 (m, 5, C-7 proton and unsaturated protons in allyl group), 4.82 (dm, 2, J=6, unsaturated protons on allyl group on C-2 carboxylate), 4.64(dm, 2, J=6, saturated protons on allyl group on C-3 carboxylate group), 4.38 (d, 1, J=13, C-4 proton), 4.04(t, 1, J=8, C-6 proton), 3.92 (d, 1, J=13, C-4 proton), 2.88 (dd, 1, J=8, 12, C-6 proton), 1.45 (s, 9, methyl protons of t-butyl group); u.v. (methanol): λ$_{max}$=345 (ε=8500); i.r. (CHCl$_3$); 3019, 1750, 1736, 1709, 1384, 1370, 1278, 1234, 1215, 1162 cm$^{-1}$;

Anal. Calcd. for C$_{19}$H$_{25}$O$_7$N$_3$: Theory: C, 56.01; H, 6.19; N, 10.31. Found: C, 56.24; H, 6.35; N, 10.10.

Preparation 5

2,3-di(Allyl Carboxylate)-7-(R,S)-[2-(Thien-2-yl)Acetamido]-8-Oxo-1,5-Diazabicyclo[3.3.0]Octa-2-ene A. Removal of Amino Protecting Group and Formation of TFA Salt 2,3-di(Allyl carboxylate)-7-(R,S)-(t-butoxycarbonylamino)-8-oxo-1,5-diazabicyclo[3.3.0]octa-2-ene 407 mg, 1 mmol) was dissolved in trifluoroacetic acid (2 ml) and the solution was stirred for 5 minutes then concentrated in vacuo.

B. Neutralization of TFA Salt

The residue from Step A was taken up in THF (5 ml) and BSTFA (1.5 ml) was added while the mixture was being cooled to 0° C.

C. Acylation of Nucleus

A THF solution (1 ml) of 2-(thien-2-yl)acetyl chloride (176 mg, 1.1 mmol) was added to the solution from Step B and the resultant mixture was stirred at 0° C. for 20 minutes. The reaction mixture was then poured into ethyl acetate and the resulting organic mixture was washed with saturated sodium bicarbonate solution, 0.2N hydrochloric acid, brine, dried over magnesium sulfate and filtered. The filtrate was concentrated in vacuo to give 700 mg of crude oily residue. The residue was chromatographed on a silica gel preparatory-scale TLC plate eluted with 1:1 hexane:ethyl acetate solution to give 270 mg, 62% yield of 2,3-di(allyl carboxylate)-7-(R,S)-[2-(thien-2-yl)acetamido]-8-oxo-1,5-diazabicyclo-[3.3.0]octa-2-ene: n.m.r. (90 MHz, CDCl$_3$): δ7.22 (m, 1, C-5 proton of thienyl group), 6.96 (m, 2, C-3 and C-4 protons of thienyl group), 6.56 (br. d, 1, J=6, amido proton), 6.20–5.60 (m, 2, C-2 proton of allyl groups), 5.60–5.10 (m, 4, C-3 unsaturated protons of allyl groups), 5.0 (m, 1, C-7 proton), 4.80 (dm, 2, J=6, C-1 protons of allyl group on C-2 carboxylate group), 4.64 (dm, 2, J=6, C-1 proton on allyl group on C-3 carboxylate group), 4.36 (d, 1, J=12, C-4 proton), 4.08 (t, 1, J=8, C-6 proton), 3.92 (d, 1, J=12, C-4 proton), 3.80 (s, 2, methylene protons of acetamido group), 2.86 (dd, 1, J=8, 12, C-6 proton); u.v. (methanol): λ$_{max}$=340 (ε=6850), 230 (ε=12,500); m.s.: Mε=431; i.r. (CHCl$_3$) 1750, 1705 cm$^{-1}$;

Anal. Calcd. for C$_{20}$H$_{22}$N$_3$O$_6$S:
Theory: C, 55.68; H, 4.91; N, 9.74; S, 7.43.
Found: C, 55.97; H, 5.21; N, 9.52; S, 7.23.

Preparation 6

2,3-di(Carboxylic Acid)-7-(R,S)-[2-(Thien-2-yl)Acetamido]-8-Oxo-1,5-Diazabicyclo[3.3.0]Octa-2-ene Triphenylphosphine (35 mg, 0.13 mmol) was added to a solution of palladium(II) acetate (6 mg, 0.026 mmol) in acetone (3 ml). The mixture was stirred until a white precipitate formed (10 minutes). An acetone solution (3 ml) of 2,3-di(allyl carboxylate)-7-(S)-[2-(thien-2-yl)acetamido]-8-oxo-1,5-diazabicyclo-3.3.0]octa-2-ene (200 mg, 0.46 mmol) was added to the mixture. After the resultant mixture became homogenous, it was cooled to 0° C. and tri(n-butyl)tin hydride (0.27 ml, 1 mmol) was added. The solution was stirred at 0° C. for 30 minutes. 1N Hydrochloric acid (1 ml) was added and the solution was stirred for an additional 10 minutes. The solution was filtered, diluted with water (30 ml), then extracted with hexane (4 X, 50 ml). The aqueous phase was separated and freeze-dried to give 170 mg of yellow powder. The powder was triturated with ethyl acetate, sonicated, centrifuged, and the recovered solid was dried in vacuo to give 2,3-di(carboxylic acid)-7-(R,S)-[2-(thien-2-yl)acetamido]-8-oxo-1,5-diazabicyclo[3.3.0]octa-2-ene: n.m.r. (90 MHz, acetone-d6) δ 7.20 (m, 1, C-5 proton of thienyl group), 6.94 (m, 2, C-3 and C-4 protons of thienyl group), 5.2–4.6 (m, 2, acetamido nitrogen proton and C-7 proton), 4.24 (d, 1, J=13, C-4 proton), 4.0–3.8 (m, 2, side chain methylene proton), 3.80 (s, 2, a C-6 proton and a C-4 proton), 3.0 (dd, 1, J=8, 12, a C-6 proton); u.v. (methanol): $\lambda_{max}$=345 ($\epsilon$=4000), 226 ($\epsilon$=7000); f.d.m.s.: (M+1)=352; i.r. (KBr): 1730, 1699, 1533, 1438, 1405, 1377, 1338, 1246, 1209, 1188 cm$^{-1}$.

Preparation 7

2,3-di(Allyl Carboxylate)-4,4-Dimethyl-7-(R,S)-(t-Butoxycarbonylamino)-8-Oxo-1,5-Diazabicyclo-[3.3.0]Octa-2-ene 4-(R,S)-(t-Butoxycarbonylamino)-3-oxo-1-(dimethylmethylene)-1,2-pyrazolidinium ylide (1.68 g, approx. 7 mmol) was dissolved in methylene chloride (25 ml) and diallyl butynedioate (1.35 g, 7 mmol) was added to the solution. The mixture was stirred at room temperature for 3 days then concentrated in vacuo. The solid was chromatographed by HPLC using a silica gel column and a 2:1 hexane:ethyl acetate gradient elution. The chromatography yielded 2.06 g, 67% yield of 2,3di(allyl carboxylate)-4,4-dimethyl-7-(R,S)-(t-butoxycarbonylamino)-8-oxo-1,5-diazabicyclo[3.3.0]octa-2-ene: n.m.r. (270 MHz, CDCl$_3$): δ 5.90 (m, 2), 5.50–5.20 (m, 4), 5.10 (m, 1), 4.90–4.50 (m, 5), 3.74 (m, 1), 3.05 (m, 1), 1.52 (s, 3), 1.46 (s, 9), 1.32 (s, 3); m.s.: M−−=435; u.v. (methanol): $\lambda_{max}$=350 ($\epsilon$=7700); i.r. (CHCl$_3$) 1749, 1707, 1436, 1385, 1370, 1274, 1231, 1215, 1161 cm$^{-1}$.

Preparation 8

2,3-di(Allyl Carboxylate)-4,4-Dimethyl-7-(R,S)-[2-(Thien-2-yl)Acetamido]-8-Oxo-1,5-Diazabicyclo-[3.3.0]Octa-2-ene A. Removal of Amino Protecting Group and Formation of TFA Salt 2,3-di(Allyl carboxylate)-4,4-dimethyl-7-(R,S)-(t-butoxycarbonylamino)-8-oxo-1,5-diazabicyclo-[3.3.0]octa-2-ene (435 mg, 1 mmol) was dissolved in neat trifluoroacetic acid (2 ml). The solution was allowed to stand for 5 minutes then concentrated in vacuo to a semi-solid. The semi-solid was dissolved in a 1:1 acetone:water solvent (6 ml) and the pH of the resultant solution was adjusted to 7 by the addition of sodium bicarbonate solution.

B. Acylation of Nucleus

The solution from Step A was cooled to 0° C. and 2-(thien-2-yl)acetyl chloride (240 mg, 1.5 mmol) was added dropwise while maintaining the pH of the solution between 6.5 to 7.5 by the addition of sodium bicarbonate solution. The reaction mixture was stirred for 30 minutes, diluted with chloroform, the layers separated and the organic layer was washed with 1N sodium carbonate, brine, dried over magnesium sulfate, filtered and concentrated in vacuo. The resulting concentrate was chromatographed on a silica gel preparatory-scale TLC plate eluted with 2:1 hexane:ethyl acetate. The chromatography yielded 290 mg, 63% yield of yellow 2,3-di(allyl carboxylate)-4,4-dimethyl-7-(R,S)-[2-(thien-2-(allyl yl)acetamido]-8-oxo-1,5-diazabicyclo[3.3.0]octa-2-ene: n.m.r. (90 MHz, CDCl$_3$): δ 7.16 (m, 1, C-5 proton of thienyl group), 6.90 (m, 2, C-3 and C-4 protons of thienyl group), 6.57 (d, 1, J=6, proton on nitrogen of acetamido group), 6.20–5.60 (m, 2, C-2 proton of allyl groups), 5.50–5.00 (m, 2, C-3 unsaturated protons of allyl groups), 4.85 (m, 1, C-7 proton), 4.72 (d, 2, J=6, C-1 proton of allyl group on C-2 carboxylate group), 4.58 (d, 2, J=6, C-1 proton of allyl group on C-3 carboxylate), 3.76 (s, 2, methylene protons of acetamido group), 3.68 (m, 1, one of the C-6 protons), 2.98 (dd, 1, J=9, 12, one of the C-6 protons), 1.49 (s, 3, protons on one of the C-4 methyl groups), 1.32 (s, 3, protons on one of the C-4 methyl groups); m.s.: M$^{\oplus}$32 459; u.v. (methanol): $\epsilon_{max}$=350 ($\epsilon$=7900); i.r. (CHCl$_3$): 1750, 1729, 1706, 1438, 1386, 1375, 1334 cm$^{-1}$.

Preparation 9

2,3-di(Sodium Carboylate)-4,4-Dimethyl-7-(R,S)-(2-(Thien-2-yl)Acetamido)-8-Oxo-1,5-Diazabicyclo-[3.3.0]Octa-2-ene Palladium(II) acetate (5 mg, 0.022 mmol) was dissolved in acetone (2 ml) and triphenylphosphine (29 mg, 0.11 mmol) was added. After approximately 5 minutes, a solution of sodium 2-ethylhexanoate (180 mg, 1.08 mmol) in acetone (1 ml) followed by a solution of 2,3-di(allyl carboxylate)-4,4-dimethyl-7-(R,S)-(2-(thien- 2-yl)acetamido)-8-oxo-1,5-diazabicyclo[3.3.0]octa-2-ene (250 mg, 0.54 mmol) in acetone (3 ml) was added. The mixture was stirred first until it was homogenous and then for an additional 4 hours at room temperature. The reaction solution was concentrated in vacuo to yield 1.2 g of non-volatile oil. The oil was triturated with diethyl ether, centrifuged, and the resultant solid was dried in vacuo. A portion of the solid material (125 mg of the resultant 185 mg) was taken up in water (40 ml). The solution was washed with methylene chloride and diethyl ether then freeze-dried to yield 110 mg of yellowish-tinted solid of 2,3-di(sodium carboxylate)-4,4-dimethyl-7-(R,S)-[2-(thien-2-yl)acetamido]-8-oxo-1,5-diazabicyclo[3.3.0]octa-2-ene: n.m.r. (90 MHz, D$_2$O): 7.18 (m, 1, C-2 of thienyl group), 6.84 (m, 2, C-3 and C-4 protons of thienyl group), 4.82 (dd, 1, J=9, 12, C-7 proton); 3.73 (s, 2, protons on methylene protons of acetamido group), 3.60-2.95 (m, 2, C-6 protons), 1.24 (s, 3, protons on one of C-4 methyl groups), 1.20 (s, 3, protons on one of C-4 methyl groups); i.r. (KBr): 1685, 1610, 1580, 1374 cm$^{-1}$.

Procedure 10

N-(t-Butoxycaronyl) (L)-Serine Trifluoroacetyl Acyl Hydrazide

N-(t-Butoxycarbonyl) (L)-serine acyl hydrazide (32.85 g, 150 mmol) was suspended in ethanol (400 ml). Ethylthio trifluorothioacetate (30 ml, 37.02 g, 234.3 mmol) was added to the suspension and the resultant mixture was stirred at room temperature for 65 hours. The solvent was removed in vacuo and the residue was dissolved in diethyl ether (160 ml). A seed crystal was added to the diethyl ether solution and the resultant crystals were collected by filtration (approx. 27 g). The filtrate was evaporated in vacuo and diethyl ether (50 ml) was added to the residue. The solids that formed on standing were removed by filtration to yield approximately 16.5 g of additional product. The two batches of solids collected by filtration were combined and recrystallized from diethyl ether (3 liters). After effecting solution, the solution was reduced to approximately 450 ml to yield (after a second crop) 41.04 g, 87% yield of N-(t-butoxycarbonyl) (L)-serine trifluoroacetyl acyl hydrazide: n.m.r. (300 MHz, DMSO-d$_6$): δ 11.5 (br. s, 1), 10.33 (s, 1), 6.84 (d, 1, J=9), 4.9 (t, 1, J=7, (OH), 4.1 (m, 1), 3.59 (br. m, 2), 1.4 (s, 9); specific rotation:

[a]$_D^{25}$ = −25.87° (10.05 mg/ml, methanol); m.p.: 143°-144° C. (first crop), 142°-144° C. (second crop).

Anal. Calcd for $C_{10}H_{16}N_3O_5F_3$: C, 38.10; H, 5.12; N, 13.33; Found: C, 38.34; H, 4.89; N, 13.16

Preparation 11

4-(S)-(t-Butoxycarbonylamino)-1-(Trifluoroacetyl)-3-Oxo-1,2-Diazolidine

N-(t-Butoxycarbonyl) (L)-serine trifluoroacetyl acyl hydrazide (3.78 g, 12 mmol) and triphenylphosphine (3.46 g, 13.2 mmol) were dissolved in THF (50 ml). To the solution was added a THF solution (10 ml) of 95% diethyl azodicarboxylate (2.42 g, 2.19 ml, 13.2 mmol). The resultant mixture was stirred at room temperature for six hours and then the solvent was removed in vacuo. The residue was dissolved in ethyl acetate (100 ml) and then the solution was washed with aqueous sodium bicarbonate solution (33 ml, 3X). The sodium bicarbonate extracts were combined, aqueous saturated brine solution (70 ml) was added and the resultant mixture was extracted with ethyl acetate (120 ml, 3X). The sodium bicarbonate solution was then layered with additional ethyl acetate (200 ml) and 1N hydrochloric acid (approx. 80 ml) was added until the sodium bicarbonate solution had a pH of 2.5. The ethyl acetate layer was separated and the aqueous layer was extracted with additional ethyl acetate (4X, 125 ml). The ethyl acetate extracts were combined, washed with saturated aqueous brine (125 ml, 2X), dried over sodium sulfate, filtered, and taken to dryness in vacuo. The resultant residue was dissolved in acetonitrile (100 ml) then the acetonitrile was removed in vacuo. Treatment of the residue with acetonitrile was repeated to yield 3.06 g, 96% yield of 4-(S)-(t-butoxycarbonylamino)-1(trifluoroacetyl)-3-oxo-1,2-diazolidine: n.m.r. (300 MHz, $CDCl_3$) δ 5.25 (d, 1, J=6), 4.81 (t, 1), 4.6 (m, 1), 4.06 (t, 1), 1.46 (s, 9); i.r. ($CHCl_3$): 1722, 1682, 1518 cm$^{-1}$; f.d.m.s. (m/e): M$^+$=297; specific rotation: [a]$_D^{25}$ = −88.14° (10.03 mg/ml in methanol);

Anal. Calcd for $C_{10}H_{14}N_3O_4F_3$: C, 40.41; H, 4.75; N, 14.14. Found: C, 40.58; H, 5.01; N, 13.92.

Preparation 12

4-(S)-(t-Butoxycarbonylamino)-3-Oxo-1,2-Diazolidine 4-(S)-(t-butoxycarbonylamino)-1-(trifluoroacetyl)-3-oxo-1,2-diazolidine (2.97 g, 10 mmol) was suspended in water (30 ml), 1N sodium hydroxide solution (20 ml, 0.8 g, 20 mmol) was added to raise the pH of the solution to 12.2 and the resultant mixture was stirred for one hour at room temperature. The pH of the mixture was adjusted to 7.2 by the addition of 1N hydrochloric acid (10 ml). Sodium chloride (13 g) was added to the solution and the mixture was extracted with chloroform (50 ml, 8X). The chloroform extracts were combined, washed with saturated aqueous sodium chloride solution (75 ml), dried over sodium sulfate, filtered, and evaporated to dryness in vacuo. Diethyl ether (100 ml) was added to the residue and then the ether was removed in vacuo to yield 0.798 g of a white solid of 4-(S)-(t-butoxycarbonylamino)-3-oxo-1,2-diazolidine: n.m.r. (300 MHz, DMSO-d$_6$); δ 9.23 (s, 1), 7.04 (d, 1, J=9), 5.24 (br. s, 1,), 4.24 (m, 1), 3.41 (t, 1), 2.88 (t, 1), 1.38 (s, 9); specific rotation: [a]$_D^{25}$ = −74.16° (10.06 mg/ml in methanol); (the compound was dried overnight at 80° C. before analysis):

Anal. Calcd for $C_8H_{15}N_3O_3$: C, 47.75; H, 7.51; N, 20.88. Found: C, 47.75; H, 7.46; N, 20.62.

EXAMPLE 3

2-(Allyl Carboxylate)-3-(Methyl Carboxylate)-7-(S)-(t-Butoxycarbonylamino)-8-Oxo-1,5-Diazabicyclo[3.3.0]Octa-2-ene

Step 1

Formation of Pyrazolidinium ylide 4-(S)-(t-Butoxycarbonylamino)-3-oxo-1,2-diazolidine (20.1 g, 100 mmol) was suspended in 1,2-dichloroethane (400 ml), 37% aqueous formaldehyde solution (0.51 ml, 3.15 g, 105 mmol) was added and the resultant mixture was stirred at room temperature for 1.5 hours to give 4-(S)-(t-butoxycarbonylamino)-3-oxo-1-(methylene)-1,2-pyrazolidinium ylide.

Step 2

Cycloaddition of Acetylene

Allyl methyl butynedioate (18.48 g, 110 mmol) was added to the mixture from Step 1 and the resultant mixture was refluxed for 6.5 hours. The volume of the reaction mixture was reduced by half in a flask fitted with a Dean-Stark trap. Hexane (200 ml) was added and the mixture was allowed to stand until an oil formed. The solvent was decanted, the oil was dissolved in ethyl acetate (300 ml) and the solution was taken to dryness in vacuo to yield 17.3 g of a foam. The foam was chromatographed using preparatory-scale high performance liquid chromatography using a silica column eluted with a gradient of 0 to 40% ethyl acetate in isooctane (8 liters). The product-containing fractions were combined to yield 1.456 g of a yellow solid. The solid was recrystallized from a mixture of ethyl acetate and hexane to yield 0.55 g of 2-(allyl carboxylate)-3-(methyl carboxylate)-7-(S)-(t-butoxycarbonylamino)-8-oxo-1,5-diazabicyclo[3.3.0]octa-2-ene: n.m.r. (300 MHz, $CDCl_3$) δ 6.00 (m, 1), 5.38 (m, 2), 5.1 (br. d, J=6), 4.86 (d, 2), 4.74 (m, 1), 4.37 (d, 1, J=13), 4.08 (t, 1), 3.91 (d, 1, J=13), 3.77 (s, 3), 2.86 (t, 1), 1.46 (s, 9); i.r. (KBr): 1751, 1710, 1687 cm$^{-1}$; u.v. (ethanol): $\lambda_{max}$=346 ($\epsilon_{max}$=8489); f.d.m.s. (m/e): M$^+$=381; specific rotation: [a]$_D^{25}$ = −481.92° (10.01 mg/ml in methanol); m.p.: 111°-113° C.;

Anal. Calcd for $C_{17}H_{23}N_3O_7$: C, 53.54; H, 6.08; N, 11.02. Found: C, 53.83; H, 6.06; N, 10.77

Preparation 13

2-(Allyl Carboxylate)-3-(Methyl Carboxylate)-7-(S)-Amino-8-Oxo-1,5-Diazabicyclo[3.3.0]Octa-2-ene Hydrochloride Salt 2-(Allyl carboxylate)-3-(methyl carboxylate)-7-(S)-(t-butoxycarbonylamino)-8-oxo-1,5-diazabicyclo[3.3.0]octa-2-ene (0.1905 g, 0.5 mmol) was added to 3M hydrochloric acid in glacial acetic acid (7 ml) and the resultant mixture was stirred at room temperature for five minutes and then taken to dryness in vacuo. The resultant yellow solid was dissolved in methylene chloride (20 ml) and the mixture was sonicated and evaporated in vacuo. The methylene chloride/sonication procedure was repeated two more times. The solid was dried in vacuo for 1.5 hours to yield to 2-(allyl carboxylate)-3-(methyl carboxylate)-7-(S)-amino-8-oxo-1,5-diazabicyclo[3.3.0]octa-2-ene hydrochloride salt.

Preparation 14

2-(Allyl Carboxylate)-3-(Methyl Carboxylate)-7-(S)-[2-(2-(Allyloxycarbonylamino)-Thiazol-4-yl)-2-(Z)-Methoxyiminoacetamido-]8-Oxo-1,5-Diazabicyclo[3.3.0]Octa-2-ene Under a nitrogen atmosphere, 2-[2-(N-allyloxy carbonylamino)thiazolo-4-yl-2-(Z)-methoxyimioacetic acid (0.1425 g, 0.5 mmol) was suspended in dried methylene chloride (5 ml). The suspension was cooled to 0° C. then 6-chloro-2,4-dimethoxy-1,3,5-triazine (0.088 g, 0.5 mmol) and N-methylmorpholine (0.0505 g, 0.5 mmol) were added. The resultant solution was stirred at 0° C. for forty minutes. Additional N-methylmorpholine (0.0505 g, 0.5 mmol) and a methylene chloride suspension (5 ml) of 2-(allyl carboxylate)-3-(methyl carboxylate)-7-(S)-amino-8-oxo-1,5-diazabicyclo[3.3.0]octa-2-ene hydrochloride salt (0.5 mmol) were added. After all the solid dissolved, the solution was stirred at room temperature for 20 hours then evaporated to dryness in vacuo. The residue was dissolved in ethyl acetate (70 ml) and water (15 ml), the layers were separated, and the ethyl acetate was extracted sequentially with 0.1N hydrochloric acid (10 ml, 3X), saturated aqueous sodium bicarbonate solution (20 ml, 3X), brine solution (20 ml,3X), dried over sodium sulfate, filtered, and evaporated to dryness in vacuo to yield 280 mg of a yellow solid. The solid was recrystallized from a mixture of methylene chloride and di(isopropyl) ether to yield 136 mg of the 2-(allyl carboxylate)-3-(methyl carboxylate)-7-(S)-[2-(2-(allyloxycarbonylamino)thiazol-4-yl-2-(Z)-methoxyiminoacetamino]-8-oxo-1,5-diazabicyclo[3.3.0]octa-2-ene: n.m.r. (300 MHz, DMSO-$d_6$) δ 12.1 (s, 1), 9.32 (d, 1, J=9), 7.43 (s, 1), 5.94 (m, 2), 5.34 (m, 4), 5.09 (m, 1), 4.83 (d, 2, J=6), 4.7 (d, 2, J=6), 4.31 (d, 1, J=13), 4.02 (d, 1, J=13), 3.88 (overlapping s and t, 4), 3.69 (s, 3), 3.18 (t, 1); u.v. (ethanol); $\lambda_{max}$=342 ($\epsilon_{max}$=8680), 264 (13,626), 209 (25,137); f.d.m.s. (m/e): M+=548, 490; specific rotation: $[a]_D^{25}$=-351.45° (10.01 mg/ml in methanol).

Anal. Calcd for $C_{22}H_{24}N_6O_9S$: C, 48.17; H, 4.41; N, 15.32. Found: C, 48.09; H, 4.41; N, 15.02.

Preparation 15 2-(Carboxylic Acid)-3-(Methyl Carboxylate)-7-(S)-[2-(2-Aminothiazol-4-yl)-2-(Z)-Methoxyiminoacetamido]-8-Oxo-1,5-Diazabicyclo[3.3.0]Octa-2-ene Hydrate Palladium(II) acetate (18 mg, 0.08 mmol) was suspended in acetone (4 ml). Triphenylphosphine (105 mg, 0.4 mmol) was washed into the suspension with additional acetone (2 ml) and tne resultant mixture was stirred at room temperature for 20 minutes. 2-(Allyl carboxylate)-3-(methyl carboxylate)-7-(S)-[2-(2-(allyloxycarbonylamino)thiazol-4-yl)-2-(Z)-methoxyiminoacetimido]-8-oxo-1,5-diazabicyclo[3.3.0]octa-2-ene (0.497 g, 0.9096 mmol) was suspended in a mixture of acetone (45 ml) and acetonitrile (15 ml) was added to the reaction suspension. This suspension was stirred at room tempurature for 35 minutes then cooled to 0° C. Tri(n-butyl)tin hydride (0.548 g, 1.81 mmol, 0.506 ml) was slowly added to the cooled suspension and the mixture was stirred at 0° C. for 30 minutes then at room temperature for 50 minutes. The mixture was cooled to 0° C. then 1N hydrochloric acid (1.82 ml, 1.81 mmol) was added. The resultant mixture was stirred at 0° C. for 10 minutes then at room temperature for 5 minutes. The mixture was filtered, water (130 ml) was added to the filtrate, and the resultant mixture was filtered through a pad of Celite ™. The filtrate was extracted with hexane (4X, 40 ml), and the aqueous layer was filtered through a pad of Celite ™ then reduced in vacuo to about 75% volume. The resultant yellow solid was removed by filtration through a pad of Celite ™ and the filtrate was extracted with ether (2X, 75 ml), concentrated in vacuo to remove any residual ether and then the resultant yellow solution was lyophilized. The lyophilized solid was dissolved in water (75 ml), filtered and then chromatographed on a preparatory-scale high performance liquid chromatograph using a $C_{18}$ reverse phase column eluted with a gradient of 0 to 10% methanol/0.5% acetic acid/water (8 liters) then a gradient of 10% to 25% methanol/0.5% acetic acid/water (8 liters) to yield 91.5 mg of 2-(carboxylic acid)-3-(methyl carboxylate)-7-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-$d_6$): δ 9.18 (d, 1, J=10), 7.24 (br. s, 2), 6.94 (s, 1), 5.02 (m, 1), 4.23 (d, 1, J=13), 3.9 (d, 1, J=13), 3.8 (overlapping t and s, 4), 3.1 (t, 1); i.r. (KBr): 1726, 1688, 1670.5 cm$^{-1}$; u.v. (ethanol): $\lambda_{max}$=328 ($\epsilon_{max}$=10, 950), 233 (16,013); f.d.m.s. (m/e): M+=425; specific rotation: $[a]_D^{25}$=-326.35° (9.83 mg/ml in methanol);

Anal. Calcd for $C_{15}H_{16}N_6O_7S\cdot H_2O$: C, 40.72; H, 4.10; N, 19.00. Found: C, 40.81; H, 3.70; N, 19.03.

We claim:

1. A compound of the formula:

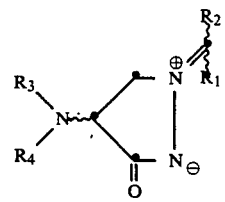

wherein:

$R_1$ and $R_2$ are the same or different and are hydrogen, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, or a group of the formula

—COOR$_5$

Wherein $R_5$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, a carboxy protecting group, or a non-toxic, metabolically-labile ester-forming group; and $R_3$ and $R_4$ are (1) taken together to form a phthalimido group; or (2) either $R_3$ or $R_4$ is hydrogen and the other of $R_3$ or $R_4$ is an amino-protecting group.

2. A compound of claim 1, wherein $R_1$ and $R_2$ are the same or different and are hydrogen, $C_1$ to $C_6$ alkyl or $C_1$ to $C_6$ substituted alkyl.

3. A compound of claim 2, wherein $R_1$ and $R_2$ are the same and are hydrogen or $C_1$ to $C_2$ alkyl.

4. A compound of claim 3, wherein $R_1$ and $R_2$ are the same and are hydrogen or methyl.

5. A compound of claim 4, wherein $R_1$ and $R_3$ are hydrogen.

6. A compound of claim 5, wherein either $R_3$ or $R_4$ are hydrogen and the other is an amino protecting group.

7. A compound of claim 6, wherein either $R_3$ or $R_4$ is hydrogen and the other is a t-butoxycarbonyl group or an allyloxycarbonyl group 8. A compound of claim 7, wherein either $R_3$ or $R_4$ is hydrogen and the other is a t-butoxycarbonyl group.

9. A compound of claim 4, wherein $R_1$ and $R_2$ are methyl.

10. A compound of claim 9, wherein either $R_3$ or $R_4$ is hydrogen and the other as an amino-protecting group.

11. A compound of claim 10, wherein either $R_3$ or $R_4$ is hydrogen and the other is a t-butoxycarbonyl group or an allyloxycarbonyl group.

12. A compound of claim 11, wherein either $R_3$ or $R_4$ is hydrogen and the other is a t-butoxycarbonyl group 13. A compound of claim 1 of the formula

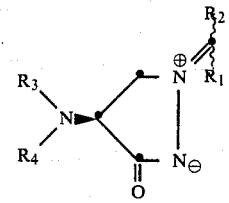

14. A compound of claim 13, wherein $R_1$ and $R_2$ are the same and are hydrogen.

15. A compound of claim 14, wherein either $R_3$ or $R_4$ is hydrogen and the other is an amino-protecting group 16. A compound of claim 15, wherein either Rhd 3 or $R_4$ is hydrogen and the other is a t-butoxycarbonyl or an allyloxycarbonyl group.

17. A compound of claim 16, wherein either $R_3$ or $R_4$ is hydrogen and the other is a t-butoxycarbonyl group.

* * * * *